US006926739B1

(12) United States Patent
O'Connor et al.

(10) Patent No.: US 6,926,739 B1
(45) Date of Patent: Aug. 9, 2005

(54) PROSTHESIS DEVICE FOR HUMAN ARTICULATIONS, IN PARTICULAR FOR THE ANKLE ARTICULATION

(75) Inventors: John J. O'Connor, 9 Beaumont Road, Oxford OX3 8JN (GB); Alberto Leardini, Bologna (IT); Sandro Giannini, Viareggio (IT); Fabio Catani, Bologna (IT)

(73) Assignees: John J. O'Connor, (GB); Instituti Orthopedici Rizzoli, (IT)

( * ) Notice: Subject to any disclaimer, the term of this patent is extended or adjusted under 35 U.S.C. 154(b) by 0 days.

(21) Appl. No.: 10/019,994

(22) PCT Filed: May 12, 2000

(86) PCT No.: PCT/IB00/00638

§ 371 (c)(1),
(2), (4) Date: Nov. 9, 2001

(87) PCT Pub. No.: WO00/69373

PCT Pub. Date: Nov. 23, 2000

(30) Foreign Application Priority Data

May 13, 1999 (IT) .............................. BO99A0253

(51) Int. Cl.⁷ ................................................ A61F 2/42
(52) U.S. Cl. ................................ 623/21.18; 623/20.29; 623/22.18
(58) Field of Search .................... 623/21.18, 20.15, 623/20.29, 20.33, 22.18, 23.41, 14.12, 23.38, 623/18.11

(56) References Cited

U.S. PATENT DOCUMENTS

| 3,872,519 A | * | 3/1975 | Giannestras et al. ...... 623/21.18 |
| 4,085,466 A | | 4/1978 | Goodfellow et al. |
| 4,309,778 A | | 1/1982 | Buechel et al. |
| 4,470,158 A | | 9/1984 | Pappas et al. |
| 4,755,185 A | | 7/1988 | Tarr |
| 5,766,259 A | | 6/1998 | Sammarco |
| 5,824,106 A | | 10/1998 | Fournol |
| 5,871,542 A | * | 2/1999 | Goodfellow et al. ...... 623/20.16 |

FOREIGN PATENT DOCUMENTS

FR    2 730 157    8/1996

* cited by examiner

Primary Examiner—Paul B. Prebilic
(74) Attorney, Agent, or Firm—Fay, Sharpe, Fagan, Minnich & McKee, LLP

(57) ABSTRACT

A prosthesis device (1) for correct replacing of the articular surfaces of the human ankle joint comprises: a first component (2) having a spherical convex articular bearing surface (5); a second component (3) having a bearing surface (6) which has a convex shape in the frontal plane, and concave sulcus in the frontal plane; and a third component (4) located between said first and second components (2, 3) and having two surfaces (7, 8) which are complementary to and engage the upper convex and the lower concave sulcus surfaces (5, 6) to be fully congruent with the components (2, 3). The three components (2, 3, 4) can be designed from the subject-specific geometry of the ligaments (9, 10). The device (1) can move under natural muscular and ligamentous control, closely restoring that of a natural joint and maintaining uniform load distribution. A prosthesis device (1) implanted according to a stated method of ensuring equal dorsi- and plantar-flexion gaps between first (2) and second (3) components, is a part of the invention.

11 Claims, 7 Drawing Sheets

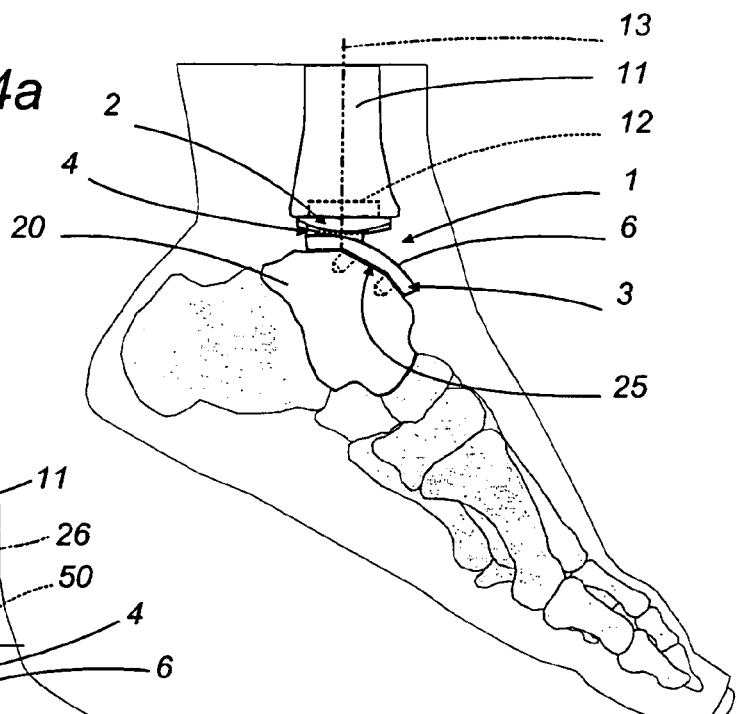
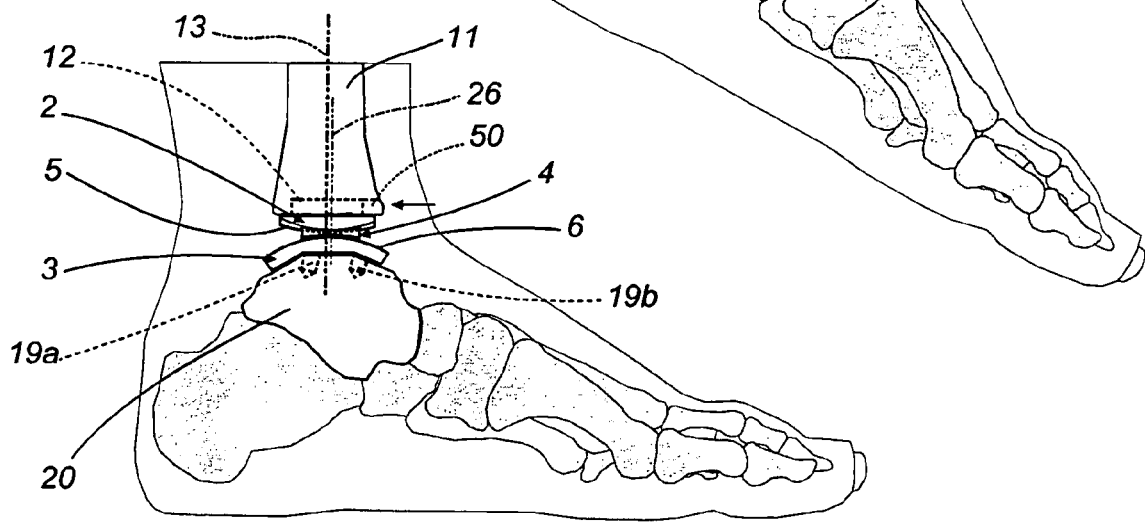
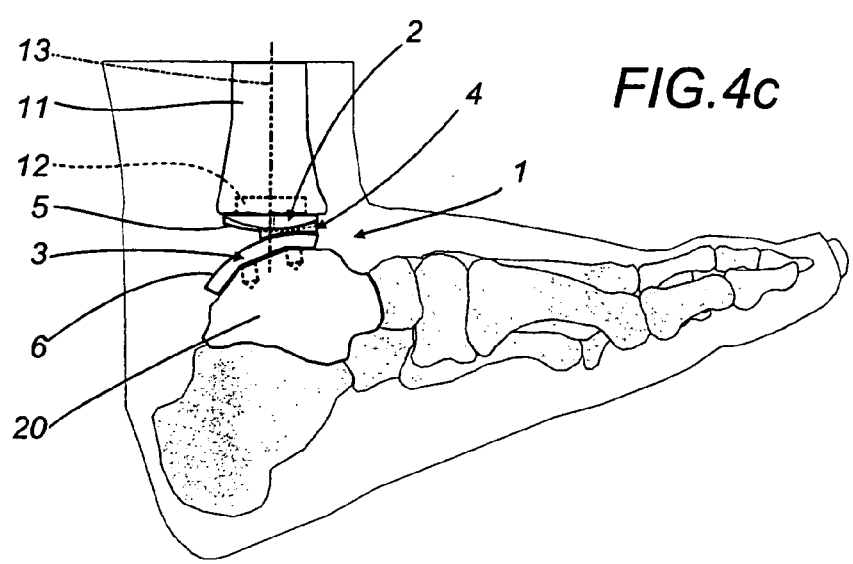
FIG.4a
FIG.4b
FIG.4c

PROSTHESIS DEVICE FOR HUMAN ARTICULATIONS, IN PARTICULAR FOR THE ANKLE ARTICULATION

TECHNICAL FIELD

The present invention relates to a total prosthetic human ankle joint and to methods for the design of subject-specific shapes and sizes of the relevant components, particularly for a three-component prosthesis with a meniscal bearing for complete congruence of the parts in all positions of the human ankle joint.

BACKGROUND ART

In total ankle replacement, the degenerated articular surfaces are removed and replaced with an artificial joint called a prosthesis. The goals are a) to relieve the pain, b) to restore the original mobility, c) to restore the original stability of the joint.

Human joint replacement design has to address the following traditional dilemma. In an articulation subjected to multidirectional loads like the ankle, an unconstrained or semi-constrained type of prosthesis that allows for the necessary axial and transverse as well as flexion/extension mobility requires incongruent contact, which however leads to inadequate load-bearing capacity. Conversely, a congruent type of prosthesis produces undesirable constraining forces that overload the anchoring system. The use of a floating bearing element could be adopted in some cases to solve the dilemma. Meniscal bearing prostheses provide for complete congruence over the entire range of positions of the joint with minimally constrained components to enable the soft tissues still to control the physiological motion of the joint. However, potential problems pertaining to the risk of subluxation and/or dislocation can be envisioned. This depends respectively on the degree of distracting stability of the joint and the degree of entrapment of the bearing element in between the bone-anchored components.

Therapy resistant ankle pain and the disadvantages of ankle arthrodesis (i.e. fusion of the two damaged surfaces) for the ankle led to the development of numerous ankle joint prostheses since the early Seventies. After the first encouraging results, ankle arthroplasty acquired a bad reputation based on many long-term follow-up clinical-radiographic studies. The frequent failures of the previous implants have been related mainly to the inadequate restoration of the original mobility and stability of the ankle complex, caused by poor knowledge of the guiding/stabilizing role played by the ligaments involved. The relative contribution of the ligamentous structures and articular surfaces of the joint in its passive and active stability, in fact, had not yet been fully understood.

Since the early Seventies, the disadvantages of ankle arthrodesis have encouraged numerous ankle arthroplasty designs. The designs devised by the pioneers (1970–1979) all featured two-component prostheses, which have been further classified as constrained, semi-constrained and non-constrained. The two-component designs have been also categorized as incongruent (trochlear, bispherical, concave-convex, convex-convex), and congruent (spherical, spheroidal, conical, cylindrical, sliding-cylindrical), according to the shape of the two articular surfaces. The former type enables a better restoration of normal joint motion but poor wear and deformation resistance due to high local stresses resulting from small contact areas and poor inherent stability. The congruent designs can be expected to provide better performance in terms of resistance to wear and surface deformation due to a better pressure distribution, but also an inadequate restoration of the characteristic three-planar rotation and articular gliding. Cylindrical or conical designs can also provide high stability since the surfaces are forced into total conformity under load, restricting motion to a single plane.

Despite the multitude of designs, to this day there are no total ankle arthroplasty designs with clinical results comparable to those achieved with arthrodesis and to those obtained with total hip and total knee replacements. Aseptic loosening of the tibial and/or of the talar components is the most frequent cause of failure, but complications include also deep infection, dehiscence of the surgical wound, lateral and/or medial subluxation of the floating meniscus, lateral talofibular joint impingement, subsidence of the talar component. The relationship between cause of failure and the etiology of the degenerative disease has been studied by many authors with a large variation of the results reported.

There are several reasons for the poor clinical results of specific prior designs, such as excessive bone resection and bearing subluxation. Common problems are antero-posterior and inversion-eversion instability of the unconstrained designs, high contact stresses, high constraint forces of the constrained designs that produce high stress at the interface between the prosthetic component and the bone interface. Considering the different types of prosthesis, the highest failure rates are shown by the constrained designs. Non-constrained designs with incongruent articular surfaces show only slightly better results. However, inherently poor wear and deformation resistance and poor stability of this type of replacement have been reported.

The more recent prosthesis designs feature three components and comprise a floating bearing, introduced to allow full congruence at the articular surfaces in all joint positions in order to minimize wear of the components while coping with the multi-axial nature of the rotation of the ankle. These designs all feature a planar and a curved surface for the floating intermediate element, to allow the characteristic internal/external rotation at the ankle joint. The floating bearing had been introduced to allow a controlled freedom of motion relative to the tibial component, allowing controlled antero-posterior as well as medial-lateral motion (see document U.S. Pat. No. 5,766,259), in such a way as to reduce wear of the surfaces and stress at the interface between the bone and the tibial component of the prosthesis. However, lateral motion is unlikely to occur at the ankle due to the high level of entrapment of the talus within the tibial mortise in the frontal plane. Moreover, no attention has ever been dedicated to understand which joint structures should enable and control this motion.

The most important aim of the present invention is in fact to include the controlling and limiting functions of the ligaments in the design of the ankle prosthesis while minimizing wear.

The limits of prior three-component designs are related to the lack of attention paid to the essential role of the ligaments in restoring the physiological kinematics of the joint. The original pattern of slackening/tightening of the ligaments should be restored to enable the physiological sliding/rolling motion of the articular surfaces, as recently discovered by the inventors. This pattern can be restored only when the shapes of the prosthetic articular surfaces and the geometry of the ligamentous structures retained are compatible, i.e. the articular surfaces move in mutual contact while maintaining some ligament fibers at a constant length. All prior three-component designs have been aimed at replicating, for the talar component, the same radius as measured in intact bones. The introduction of a third component and of a different shape for the tibial mortise surface (of a planar type) would instead have entailed abandoning anatomical criteria for the design and should have led to closer investigation of the perfect compatibility of all passive structures.

The design of an ankle joint prosthesis should aim either to replicate exactly the complete original anatomical geometry of both the ligamentous structures and the articular surfaces, or to restore the original compatible function of the ligaments and of the articular surfaces introducing the floating component, regardless of the original anatomical shapes of the articular surfaces. In the former option, the slight incongruity between the tibial and the talar articular surfaces should be restored, and its lack can be the cause of the failure of cylindrical and spherical designs. In the latter option, instead, any attempt to imitate the anatomical shapes of the articular surfaces characteristic of intact bones should be abandoned. The confusion between these two options (meniscal bearing designs but with articular surfaces approximating anatomically-shaped curves) is thought to be the problem inherent in the three-component prosthesis designs proposed heretofore, which proves the relevance and the originality of the present invention. The three-component meniscal bearing designs of the prior art (U.S. Pat. No. 5,766,259, STAR®) have claimed to have simulated the original articulating surfaces of the ankle joint to enable proper movement of the parts. We believe instead that when a third component, not present in the natural joint, is introduced in the joint and when the natural concave shape of the tibial mortise is replaced with a planar surface, the design of the articular surfaces should be aimed only at restoring the original functions, regardless of the original anatomy of the bones.

Furthermore, all the previous three-component prosthesis designs (see documents U.S. Pat. No. 4,470,158, U.S. Pat. No. 4,755,185, U.S. Pat. No. 5,766,259, U.S. Pat. No. 5,824,106, STAR®) do in fact allow for internal/external rotation (about the longitudinal axis of the tibia) at the interface between the floating bearing and the tibial component, but do not allow ab/adduction (about the antero-posterior anatomical axis), as it occurs in the intact human ankle complex (ankle and subtalar joints) to be replaced. The problems inherent in these designs also relate to the expected poor stability in the transverse plane due to the planar-to-planar interface between two of the components, and lastly to the small, projecting constraint elements used in prior designs to guide the bearing core (pins, incisions and grooves, in documents U.S. Pat. No. 5,824,106 and U.S. Pat. No. 4,755,185).

The proposed aim of restoring the physiological functions of the ligaments during the motion of the replaced joint and in resistance to lesions has been presented only to a limited extent in prior ankle replacement designs. One of the main innovative elements of the present invention is its original introduction of the role of the ligaments in controlling and limiting the movement of the ankle joint complex.

DISCLOSURE OF INVENTION

The present application is an improvement of a previous patent application (U.S. Pat. No. 4,085,466), devised for the human knee joint and developed herein for the ankle joint.

In order to restore the natural articular load bearing pattern, an ideal human joint prosthesis should reproduce the physiological type of motion and the original pattern of ligament slackening/tightening. Previous studies by the present authors on intact cadaver ankle joints (Leardini, A. and O'Connor, J. J. and Catani, F. and Giannini, S. Kinematics of the human ankle complex in passive flexion—a single degree of freedom system, J Biomechanics 1999, 32(2):111–118. Leardini, A. and O'Connor, J. J. and Catani, F. and Giannini, S. A geometric model for the human ankle joint, J Biomechanics 1999, 32, (6)) seem to be qualitatively consistent with what has been already observed in the knee joint. The type of motion is complex, including sliding as well as rolling between the articular surfaces.

The axis of rotation changes, and in any one position it depends both upon the geometry of the articular surfaces and the direction and magnitude of the tensile forces developed in the associated muscles and ligaments. It has been shown that under passive conditions, the articular surfaces and the ligaments describe a unique envelope for the position of the axis of rotation. The changing positions of the axis of rotation suggests that the hinge-like concept for the ankle joint is an oversimplification and does not reflect the actual kinematic pattern of motion. Several studies have also described a more isometric pattern of rotation for the calcaneofibular and tibiocalcaneal ligaments in comparison with all the others (Colville, M. R. and Marder, R. A. and Boyle, J. J. and Zarins, B., Strain measurement in lateral ankle ligaments, Am J Sports Med 1990, 18(2), 196–200; Bruns, J. and Rehder, U., Ligament kinematics of the ankle joint, Zeitschrift fur Orthopadie und Ihre Grenzgebiete 1993, 131(4), 363–369). A few recent studies also claim an anterior shift of the contact area at the tibial mortise during dorsiflexion (Kitaoka, H. B. and Kura, H. and Luo, Z. P. and An, K. N., Contact features of the ankle joint, Proceedings of 42nd Annual Meeting of Orthopaedic Research Society, Atlanta (Ga.), 19–22 Feb. 1996, 396). In conclusion, it has been shown that a) the most anterior fiber of the calcaneofibular and of the tibiocalcaneal ligaments control and guide ankle motion in its predefined and preferential passive path, whereas the other ligament fibers limit but do not guide motion; b) the axis of rotation moves anteriorly and superiorly during dorsiflexion; c) the contact area moves anteriorly on the tibial mortise during dorsiflexion. Therefore, as with the knee, the slackening and the tightening of the ankle ligaments may be explained in terms of their instantaneous positions with respect to the moving axis of rotation. Studies by the authors have recently demonstrated this pattern of motion and the close relationship between the geometry of the ligaments and the shapes of the articular surfaces of the ankle.

These observations imply that the articular surfaces of the bone segments in contact must fulfil the requirement that they can be moved passively in mutual contact while fibers within the calcaneofibular and tibiocalcaneal ligaments remain at constant length. For ankle joint replacement, it is suggested that the shapes of the articular surfaces of the prosthesis components must be compatible with the geometry of the retained ligamentous structures. In other words, the articular surfaces and the ligaments work together to allow and control joint movement: the articular surfaces can slide and roll on each other and the ligaments can rotate about their origins and insertions on the bones without resistance and therefore without tissue deformation (surface indentation or ligament stretch). The isometric rotation of the two ligaments defines also the position of the axis about which dorsi/plantarflexion occurs. In passive rotation, the motion of the talus/calcaneus segment is therefore constrained, but not cylindrical with a fixed axis of rotation. Both the existing constrained cylindrical and unconstrained ball-and-socket prosthesis designs therefore do not properly restore the natural kinematics pattern of the intact ankle joint.

When the geometry of the two isometric ligaments is known and when the shape of one articular surface is given, the shape of the complementary surface of the other articular segment can be deduced in order for it to be compatible with ligament isometry: in order to avoid the interpenetration or separation of the two bones, the normal at the contact point on the complementary surface must pass through the axis of rotation of the relative motion.

Both a two-component prosthesis with articular surfaces that are anatomically-shaped, and therefore slightly non-congruent in the sagittal plane, and a three-component prosthesis with full congruence could be devised. However, in the former option, a higher wear rate is expected because of the higher contact stress due to the not exact fit of the two components. Moreover, because of the need to achieve overall surface/ligament compatibility in the replaced joint, the accuracy required for implanting two components becomes too critical for the overall success of the implant and the risk of erroneous positioning can be high.

However, experimental observations can also call for a three-component prosthesis for ankle joint replacement. An intermediate meniscal bearing component would allow for a large contact area throughout the range of dorsi-plantarflexion and also for restoration of the original mobility in terms of sliding and rolling motion as exhibited by the intact joint. The prosthesis therefore consists of a tibial and a talar component, together with an intermediate ultrahigh molecular weight polyethylene (UHMWPE) meniscal bearing component to be inserted in between, with the articulating surfaces fully congruent to those of the surfaces of the components anchored to the bones. The thickness of the meniscal bearing component can be selected to be the most appropriate to restore the original tensioning pattern of the ligaments: thicker or thinner bearings would involve joint rigidity or laxity respectively. As in the intact joint, the articular surfaces do not constrain the relative motion of the bone segments but merely allow the unconstrained meniscal bearing component to perform the motion directed by the ligamentous mechanism. The three-component meniscal bearing design has also the advantage that it can accommodate for surgical technique errors entailing the erroneous positioning of the prosthesis components.

Lastly, it has been observed that when total ankle replacement is performed, the subtalar joint complex is frequently affected too. Total ankle replacement certainly does have to cope with an affected ankle (talocrural) joint but also, very often, with an affected subtalar (talocalcaneal) joint, and therefore it should be aimed at restoring the function of both joints.

The present invention provides a three-component prosthetic joint device, comprising a first component having an articular bearing surface that is generally curved in a convex manner, a second component having an articular bearing surface that is generally curved in a convex manner in the sagittal plane and curved in a concave manner in the frontal plane, and a third component having two articular bearing surfaces in back-to-back disposition and with individual shapes that are substantially complementary to the articular surfaces of said first and second component. When the invention is used in an ankle joint endoprosthesis, the first and the second component are to be secured respectively to the tibia and to the talus with the articular surfaces of these components in mutually opposite disposition, and the third component is to be located therebetween to serve as a meniscal component with its articular bearing surfaces in respective contact with those of the aforesaid components.

DESCRIPTION OF THE DRAWINGS

The technical features of the invention, according to the aforesaid aims, can be clearly noted from the content of the claims set out below and its advantages shall become more readily apparent in the detailed description that follows, made with reference to the accompanying drawings, which show an embodiment provided purely by way of non limiting indication, in which:

FIGS. 4a, 4b, 4c are an overall representation of the prosthesis device when implanted in the joint between the shank and the foot, schematically showing its characteristic kinematics;

With reference to FIGS. 1 and 2, the reference number 1 globally indicates an ankle prosthesis device comprising three components: a first distal tibial component 2, made of metal; a second proximal talar component 3 with metallic dome, and a third component 4 interposed to the first two components 2, 3 and embodied by a plastic or UHMWPE meniscal bearing, which is provided with bearing surfaces 7, 8 totally congruent with corresponding opposite articular metal surfaces 5, 6 of the tibial component 2 and of the talar component 3.

Figure 1:
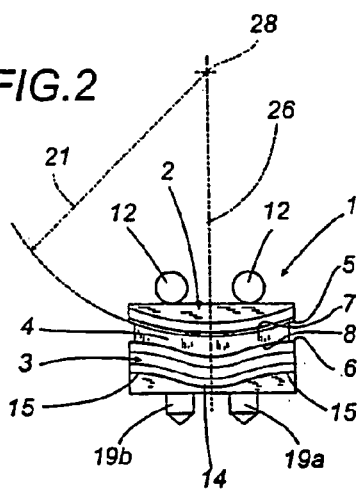
FIGS. 1 and 2 are respectively an overall view in the sagittal plane (anterior direction of the prosthesis on the right hand side) and in the frontal plane of a prosthesis device according to the invention.

To be compatible with the isometric rotation of the anatomical ligament fibers 9, 10, (FIG. 3), the tibial and talar surfaces 5, 6 can be of any shape, but when the shape of one articular surface 5 is given, the shape of the complementary surface 6 of the other component is deduced accordingly.

To minimise the resection of the talus bone 20, the talar component 3 should be convex in the sagittal plane. It has been found that curved, convex, multicentric and multiradial shapes of the articular surface 6 of the talar component 3 can be compatible planar, concave, or convex shapes of the articular surface 5 of the tibial component 2.

The selection of a convex spherical shape with radius 21 for the articular surface 5 of the tibial component 2 (as FIGS. 1 and 2 clearly show) was made because of the better degree of antero/posterior and medial-lateral entrapment of the bearing element 4 with the associated smaller risk of subluxation and dislocation. It also allows ab/adduction motion in the frontal plane as well as the internal/external rotation.

So, given a convex circular arc in the sagittal plane of the articular surface 5 of the tibial component 2, together with the geometry of the two ligament fibers 9, 10, a series of contact points for the optimal dome of the articular surface 6 of the talar component 3 are deduced. For the total conformity of the articulating surfaces 6, 8, between the talar 3 and meniscal bearing 4 components, a circular arc that best approximates these points is then adopted. This best fit values for the radius 23 of the dome-shaped articular surface 6 of the talar component 3 in the sagittal plane are considerably greater than those of prior three-component designs, which in fact aimed to imitate the normal anatomical shapes of the trochlea tali while replacing the concave tibial mortise with a flat component.

Figure 3A:
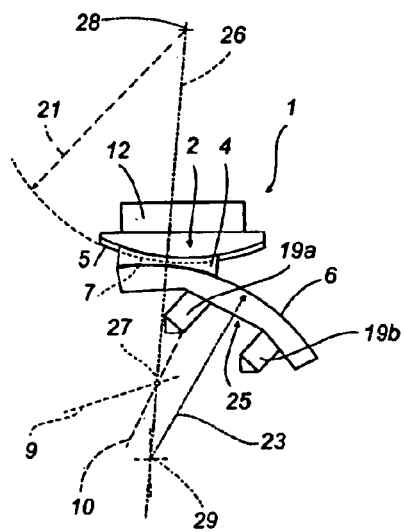
FIGS. 3a, 3b, and 3c schematically show the mechanism of relative motion expected between the prosthesis components as guided by the ligament fibers in an implanted joint in three characteristic positions: in maximal plantar-, neutral and maximal dorsi-flexion respectively.
Figure 3B:
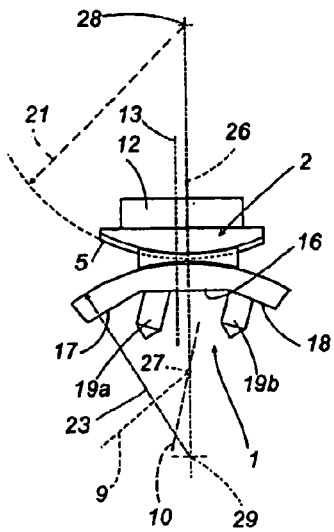
Figure 3C:
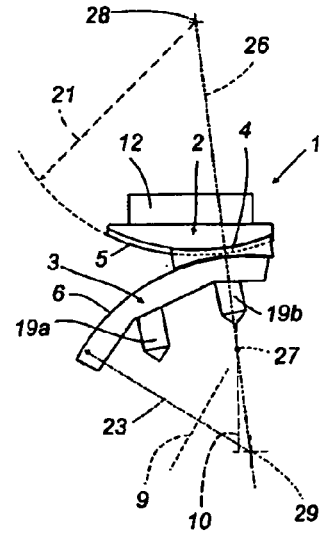

It has been found that only with a much more ample arc radius 23 for the talar component 3, can the articular surface 6 perform the characteristic pattern of sliding and rolling during ankle flexion, which involves a significant antero-posterior displacement of the meniscal bearing 4 both relative to the tibial component 2 and to talar component 3 (FIGS. 3*a*, 3*b* and 3*c*).

Therefore, the criteria pertaining to the restoration of the original kinematics pattern and to the minimization of the risk of dislocation for the meniscal bearing 4 are both met. FIGS. 3*a*, 3*b* and 3*c* and 4*a*, 4*b*, 4*c* schematically show, with different dimensional scales, in the sagittal plane of the tibia 11, the kinematics of the ankle once it has been replaced with a prosthesis embodied by the device 1 according to the invention.

During flexion, the talar component 3 slides in the sagittal plane on the meniscal bearing 4, which at the same time rotates about the center of curvature of the arc of the tibial component 2. This rotation involves an antero-posterior translation of the meniscal component 4 along the tibial component 2. With ankle joint motion constrained by this type of mechanism, the estimated elongation of the two ligament fibers 9, 10 is less than 0.2% of resting length. Hence, the design allows for the restoration of the original pattern of ligament slackening/tightening and also for the existence of large contact areas throughout the flexion range. When the two ligament fibers 9, 10 are taken to rotate isometrically about their points of origin on the tibia/fibula segment 11, the point 27 (FIG. 3) at which the directions of the two ligaments cross is the instantaneous axis of joint rotation.

The tibial component 2 consists of a highly polished spherical articular surface 5 (FIGS. 1 and 2) with two cylindrical bars 12 covered with a porous coating, which bars are positioned on the upper surface 2*a* and are provided for anchoring the tibial component 2 to the subchondral bone of the distal tibia 11.

The articular surface 5, the lower surface of the tibial component 2, is a convex spherical arc, with a center of curvature 28 in the tibial body (FIG. 3*b*). The articular surface 6, the upper surface of the talar component 3, is a convex arc in the sagittal plane, with a center of curvature 29 in the talar body. In the neutral position of the ankle joint (FIG. 3*b*), the line 26 joining the centers 28 and 29 of the tibial and talar arcs 5, 6 must be situated at the same antero-posterior position of the instantaneous axis of rotation 27, at the intersection of the two isometric ligament fibers 9, 10 (FIG. 3). This line 26 is located, in the sagittal plane, slightly forward relative to the longitudinal axis 13 of the tibia 11 (FIGS. 1, 3*b* and 4*b*). This positioning is due to the fact that the axis of joint rotation moves in the sagittal plane during dorsi/plantarflexion, and in the neutral position of the ankle it is located slightly forward of the longitudinal anatomical axis of the tibia 11.

The talar component 3 consists of a metal shell. The upper surface 6, which identifies with the aforementioned articular surface, is partly anticlastic, having two mutually transverse curvatures, in opposite directions, as the surface of a saddle. The upper surface 6 is a revolution surface, generated by rotating a generatrix curve about a medial-lateral fixed axis, orthogonal to the sagittal plane of FIG. 1, i.e. belonging to the frontal plane of FIG. 2.

Figure 2:
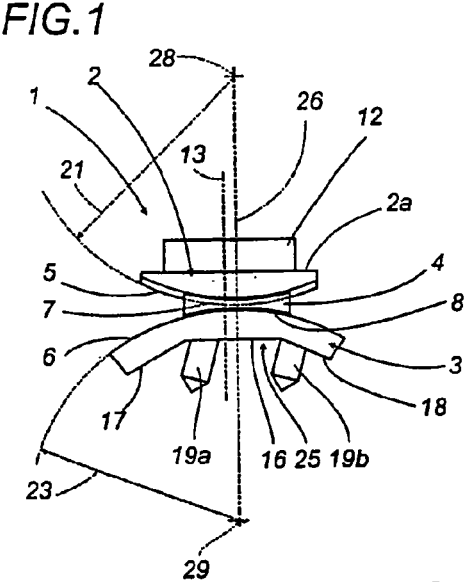

The radius 23 of this arc in the sagittal plane (FIGS. 1 and 3*b*) is, however, different from that 21 of the tibial component 2 in the same plane, and calculated in such a way as to be compatible with the isometric rotation of the fibers 9, 10 of the guiding ligaments. The generatrix curve is concave in the frontal plane (FIG. 2), presenting a concave circular arc, the sulcus 14, between two convex circular arcs 15. The upper surface—coinciding with the articular surface 6—therefore shows a circular convex arc in the sagittal plane (FIG. 1), and has a concave sulcus when seen in the frontal plane (FIG. 2).

When the prosthesis is in neutral position (FIG. 3*b*), the arc 6 in the sagittal plane is slightly longer posteriorly because of the larger range of ankle motion in plantarflexion (FIG. 4*a*) than in dorsiflexion (FIG. 4*c*), both in the natural and in the replaced joint, constituting the subject of the present invention.

On the lower surface 25—in contact with the talus 20—of the talar component 3, three cuts 16, 17, 18 are made for anchoring to the talar bone 20: a superior talar cut 16, orthogonal to the longitudinal axis 13 of the tibia 11 when the ankle is in neutral position, and anterior 18 and posterior 17 chamfer cuts.

On this surface 25 with three cuts 16, 17, 18, two cylindrical pins 19*a*, 19*b* are made as indicated on the Figures to allow for better anchoring to the talus bone 20. One of the two pins 19*a* is on the superior horizontal surface, that identifies the upper talar cut 16 and is located slightly to the rear and to the right hand side. The second pin 19*b* is on the anterior chamfer cut 18, on the left hand side.

Both pins 19*a*, 19*b* are inclined slightly to the rear for easier implantation of the talar prosthesis device 1 which is normally performed with an anterior surgical access, when the ankle is in the maximal plantarflexion position (as that in FIG. 4*a*).

Given the convex arcs in the sagittal plane of the tibial component 2 and talar component 3, the floating meniscal component 4 positioned between the components 2, 3 themselves is so shaped as to have complementary concave upper 7 and lower 8 surfaces, fully congruent with the corresponding tibial and talar components 2 and 3 of the device 1 of the prosthesis in all positions of the joint.

The convex spherical shape of the tibial component 2 enables a better degree of antero/posterior (FIG. 1) and medial-lateral (FIG. 2) entrapment of the bearing element 4. The overall degree of antero-posterior entrapment is in fact the sum of the tibial and talar entrapments associated to the increase in the thickness of the meniscal bearing 4.

The entrapment of the meniscal bearing component 4 is also affected by its antero-posterior length, this length being only limited by the risk of impingement and overlapping relative to the tibial and talar components 2 and 3 in its antero-posterior run during ankle flexion.

Because of the physiological longer range in plantarflexion than in dorsiflexion and because of the more likely dislocation in the anterior rather than in the posterior direction, the meniscal bearing component 4 can be longer posteriorly and hence asymmetric relative to the line 26 of the centers 28, 29 of the tibial and talar arcs 5, 6.

Ankle joint stability in the transverse plane would therefore also benefit from a double concave shape of the articular surfaces 7, 8 of the meniscal bearing 4. This design provides better resistance to antero-posterior and side-to-side translations than a planar meniscal-tibial interface of the prior art (STAR®, Buechel-Pappas®, Albatros®, U.S. Pat. No. 5,766,259).

In the frontal plane the total conformity of the tibial component 2 with the meniscal bearing component 4 is guaranteed by a ball-and-socket articulation. The floating meniscal component 4 has a concave spherical upper surface 7, complementary to the convex spherical tibial surface 5. The lower surface 8 of the meniscal component 4 totally conforms with the sulcus 14, 15 of the talar component 3. For medial-lateral stability, both the talar and the meniscal component 4 (lower articular surface 8) have a shallow sulcus 14 in the frontal plane.

The consequences of all these arrangements are that:

1) The interfaces between the tibial 2 and meniscal 4 components, and between the meniscal 4 and talar 3 components are both capable of independent relative movement by virtue of the complementary nature of the two pairs of coupled surfaces 5, 7; 6, 8. More specifically, the tibial 2 and meniscal 4 components are capable of mutual rotation about three orthogonal axes passing through the center 28 of the spherical arc 5 of the tibial component 2. The deriving ability to perform relative motions between the tibial 2 and talar 3 components is accordingly extensive and can include rolling, gliding, twisting, and combinations thereof, such as they take place in the natural ankle joint complex.

2) These shapes of the bearing surfaces 5, 6 of the tibial 2 and talar 3 components can reproduce the natural pattern of relative motion of the corresponding bony segments even though the shapes of the natural tibial and talar articular surfaces are not reproduced exactly. Therefore, the mechanical interactions between the shapes of the surfaces 5, 7; 6, 8 and the forces in the surrounding muscles and ligaments and particularly in the related ligament fibers 9, 10 which control the stability of the joint, will be physiological as well.

3) All relative positions of the components once implanted, under passive conditions, are obtained as positions of minimum stored energy shared among the ligamentous structures of the joint. The shape of the three components 2, 3, 4 was designed to allow relative motion without resistance through mutual sliding without separation or inter-penetration, while the fibers 9, 10 of the isometric ligament rotate about their origins and insertion points without stretching or slackening. No input of energy is expected to be necessary to displace the replaced joint along this neutral passive path because no tissue deformation is necessary.

4) In particular, to obtain this series of minimum energy positions between the tibial 2 and talar 3 components, given that the talar component 3 is guided by the ligaments to slide forward while rolling backward with respect to the tibial component 2 during plantarflexion and to slide backward while rolling forward during dorsiflexion, the floating meniscal element 4 must slide backward on the tibial component 2 during plantarflexion and forward during dorsiflexion.

5) The complementary nature of the coupled surfaces of the three components 2, 3, 4 is such that a relatively uniform distribution of surface pressure of small magnitude is achieved in all the articular positions, and thus in all the relative positions of these components, as to expect a low wear rate for the prosthesis components.

6) The meniscal component 4 is entrapped between the tibial 2 and talar 3 components by virtue of the complementary convex and concave shape respectively of the coupled surfaces 5, 7 of the tibial 2 and meniscal 4 components and of the complementary partly anticlastic shape of the engaged surfaces 8, 6 of the meniscal 4 and talar 3 components.

7) The interface between tibial component 2 and the meniscal bearing 4 is a ball-and-socket joint, providing three degrees of rotational movement. A further degree of freedom is allowed at the interface between the meniscal bearing 4 and the talar component 3, when the former component can slide congruently on the latter along the sulcus 14, 15 which extends along the dome of the talar component 3 mostly antero-posteriorly. Dorsi/plantarflexion with the coupled anterior/posterior rolling is allowed at the meniscal bearing 4—talar component 3 interface. Internal/external rotation and ab/adduction are allowed at the meniscus 4—tibial 2 spherical interface. Pure translations in the transverse plane are inherently resisted.

8) The implantation of the two bone-anchored components 2, 3 has to be carried out most carefully. The center 28 of the tibial lower spherical arc 5 and the center 29 of the talar upper arc 6 must lie on the same vertical line 26 in the sagittal and frontal plane (FIGS. 1, 2 and 3b). Moreover, the third component 4 should be selected from a wide range of different thicknesses to ensure that there is neither undue laxity nor stretching in the fibers 9,10 of the ligaments such as would otherwise render the prosthesis respectively unstable or rigid.

9) It is here thought that the tibial 2, talar 3 and meniscal bearing 4 components will all have to be made in a number of dimensions to accommodate patients of different size. The number and dimension of different sizes does not constitute a limitation of the present invention. Because of its strategic importance in restoring original joint function, the meniscal bearing component 4 should also be made in various thicknesses. The step between different thicknesses can even be very small but in any case it should be large enough to allow surgeons to detect differences in articular mobility and stability during the operation. Considering that previous investigations on human joint prostheses designed according to very similar criteria (Wear of congruent meniscal bearings in unicompartmental knee arthroplasty: a retrieval study of 16 specimens; Psychoyios V, Crawford R W, O'Connor J J, Murray D W; J Bone Joint Surg Br 1998 November;80(6): 976–82) have shown that the mean rate of penetration of the meniscal component 4, which included the effects of wear at both upper and lower surfaces, can be as small as 0.01 mm per year, it is here suggested that the minimum thickness of the third component 4 can even be just a few millimeters.

Development of the invention since its initial conception has shown that, while a variety of potentially advantageous forms are possible within the more general scope of the invention, the above consequences can result from a convex tibial 5 and partly anticlastic-talar 6 surfaces. However, they could also result from a relatively simple form of the invention in which the coupled talar 6 and meniscal 8 surfaces are part-spherically or -cylindrically shaped, and the engaged bearing surfaces 7,5 of the meniscal 4 and tibial 2 components are planar. Even a two-component prosthesis could be able to assist the joint in reproducing the original pattern of ligament slackening/tightening.

The relevance of this general application of the invention is based on a particular view of the form and function of the passive structures of the joint, these elements being the articular surfaces 5, 7, 6, 8 and adjacent ligaments. This view holds that, during the passive motion of the joint, the articular surfaces 5, 7, 6, 8 serve to maintain the fibers 9, 10 of the ligaments at a constant length and that the ligaments themselves act in such a way as to maintain these articular surfaces in contact. The articular surfaces 5, 7, 6, 8 serve predominantly to transmit compressive forces, and the ligaments and the muscle tendons to control and limit the surface movements while themselves serving to resist and transmit tensile forces. Thus, there is interdependence between all the elements of a joint, and this interdependence is vital to the overall performance of a natural joint having incongruent surfaces which can provide little inherent stability.

The advantages and novelty of the illustrated device 1, with respect to prior designs can be listed as follows:

the multiaxial pattern of movement of the natural ankle joint (FIG. 4) can be closely simulated without significant distortion of the natural controlling and stabilising mechanism, while maintaining a uniform distribution of surface pressure throughout the device 1 and along the entire articular range. Because of the convex shape of the tibial component 2 and of the necessary compatibility of the articular surfaces (5, 7; 6, 8) with the isometric rotations of the ligaments 9, 10, this natural movement is obtained with an arc of curvature of the talar component 3 that is significantly different from that of the natural anatomical shape, and thus from that of all designs of the prior art;

the device 1 features totally conforming surfaces in both the tibial 2—meniscal bearing 4 and meniscal bearing 4—talar 3 component articulations in all the positions of the joint, obtained by means of the antero-posterior sliding of the meniscal bearing 4 on both components during dorsi/plantarflexion as guided by the ligamentous structures of the joint complex;

because fully congruent meniscal bearings 4 have shown a very small wear rate in other human joint prosthesis designed with the same criteria, the thickness of the polyethylene meniscal bearing 4 can also be very small, thereby minimizing the overall thickness of the prosthesis and hence of the bone section to be removed both with the cuts 16, 17, 18 and with cut on the tibia;

a convex shape of the tibial component 2 improves the level of antero-posterior entrapment of the meniscal bearing component 4, with independent and cumulative levels of entrapment, lower for the talar component 3 and upper for the tibial component 2;

medial-lateral entrapment of the meniscal bearing 4 is also guaranteed by the sulcus 14 running on the dome of the talar component 3, avoiding the sharpened limiting interfaces as used in the prior art to prevent dislocation and separation (between ribs and grooves in STAR®; lug and cutout in U.S. Pat. No. 5,824,106, even a system of interlockable flanged grooves in U.S. Pat. No. 4,755,185), which certainly entail a high risk of wearing;

unlike all previous three-component designs, the subject device 1 also allows for joint rotations about an antero-posterior axis passing through the center of curvature 28 of the articular surface 5 (FIG. 2), together with rotations about the vertical axis 26 at the tibial 2—meniscal bearing 4 interface. This is particularly important when considering that the device should enable the characteristic motion of the entire ankle complex, comprising both the ankle and subtalar joints, as the latter is frequently affected when the former is so damaged as to make the joint replacement necessary;

unlike all previous two-component cylindrical and ball-and-socket designs the axis of joint rotation 27 is not fixed as imposed by the congruity of the articular surfaces, but rather is able to move relative to both tibial 11 and talar 20 bones to assist the joint in performing the original pattern guided by the isometric rotation of certain ligament fibers 9, 10 (FIGS. 3*a*, 3*b* and 3*c*).

In order to restore the original compatibility between articular surfaces and ligaments at the human ankle joint, not only should the prosthesis components 2, 3, 4 be designed according to the criteria set out above, but should be implanted in their definitive position with great care and precision.

Methods and directions for implanting therefore are also part of the present invention, necessary and integrating the prosthesis device 1.

Figure 5A:
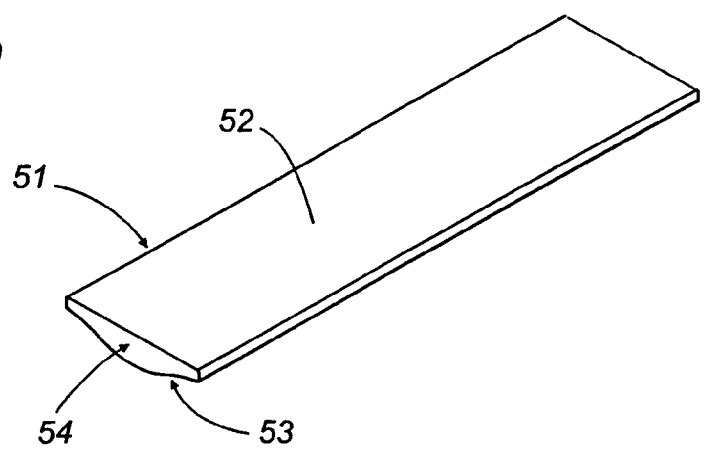
FIGS. 5a and 5b show the so called 'gap-gauges', special elements employed for executing the methods for implanting the prosthesis device in to the bones by series of measurements and cuts.
Figure 5B:
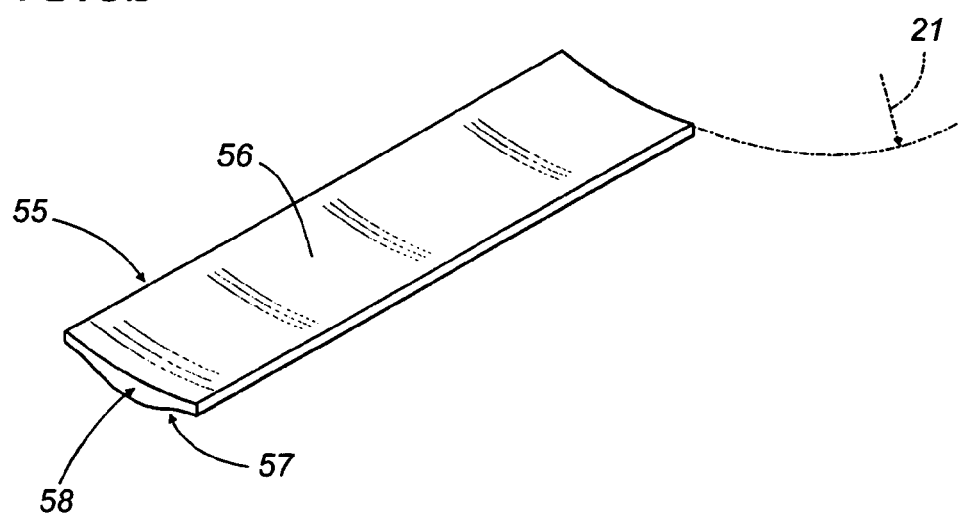
Figure 6A:
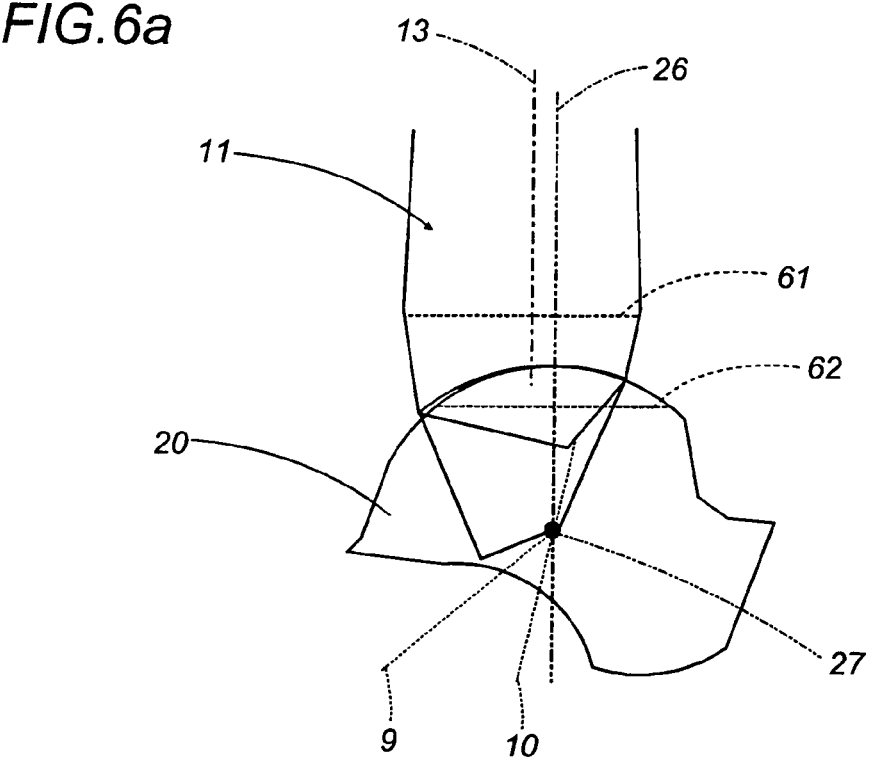
FIGS. 6a) through 6h) are a schematic representation of the main phases of a method for implanting the prosthesis device.
Figure 6B:
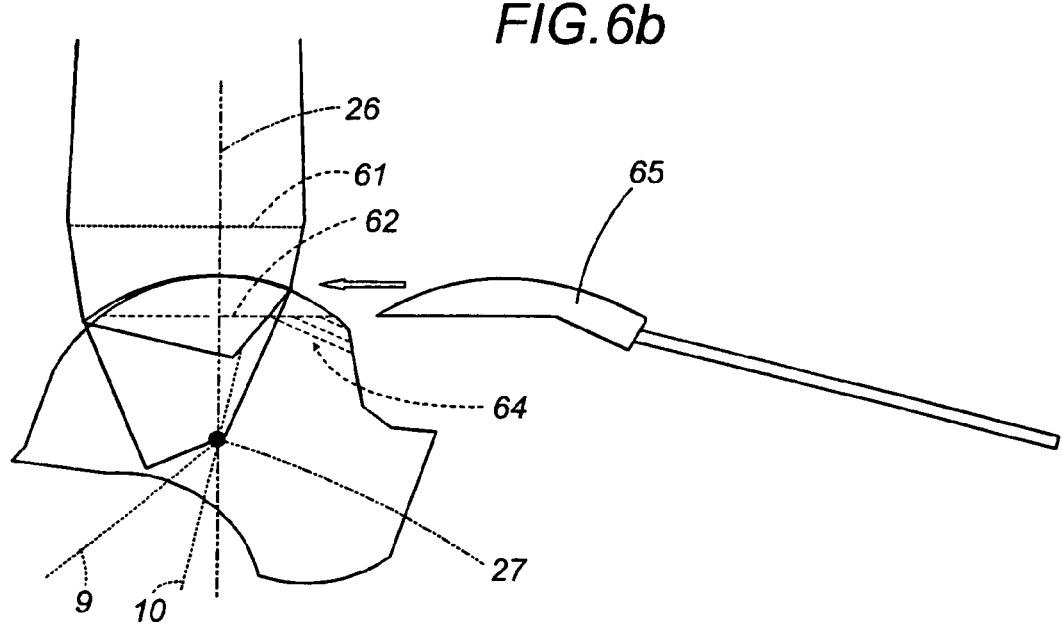
Figure 6C:
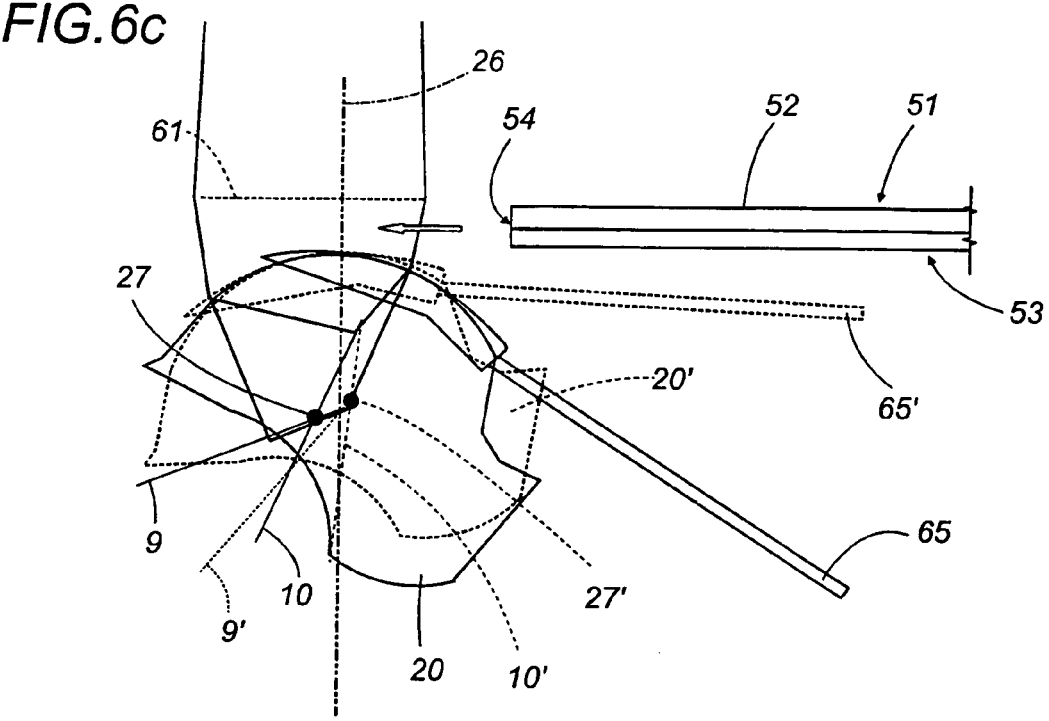
Figure 6D:
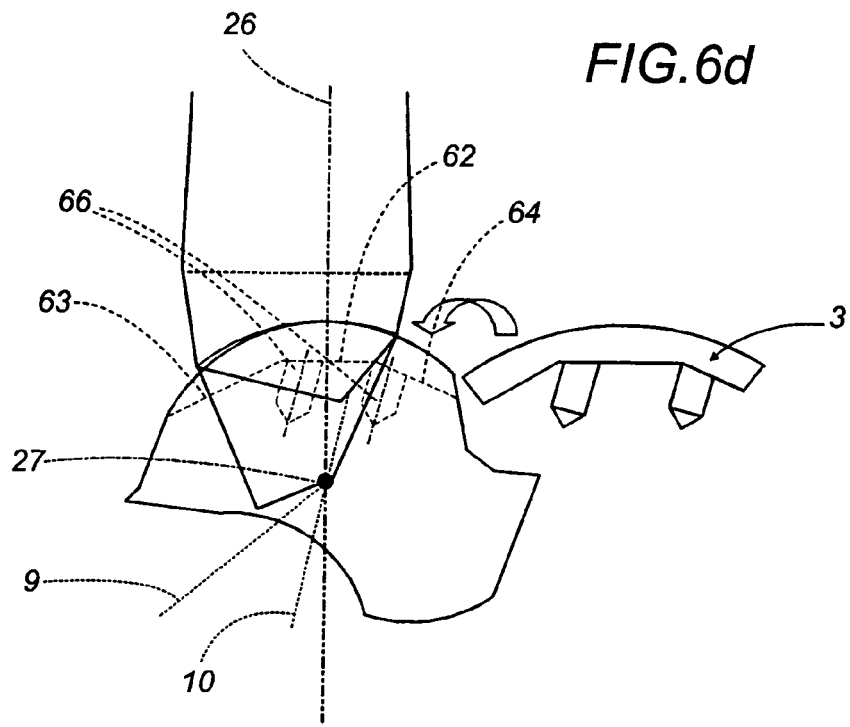
Figure 6E:
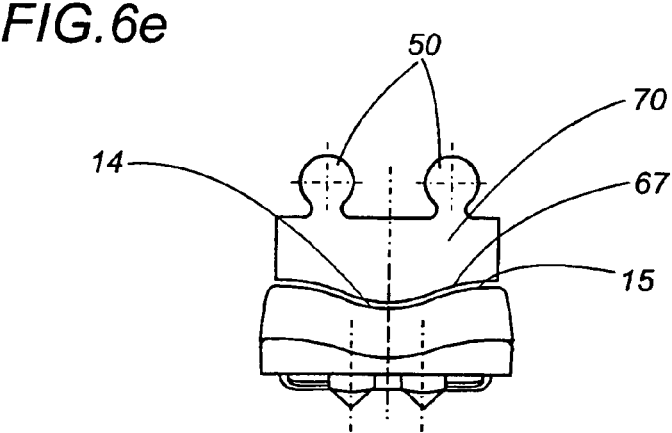
Figure 6F:
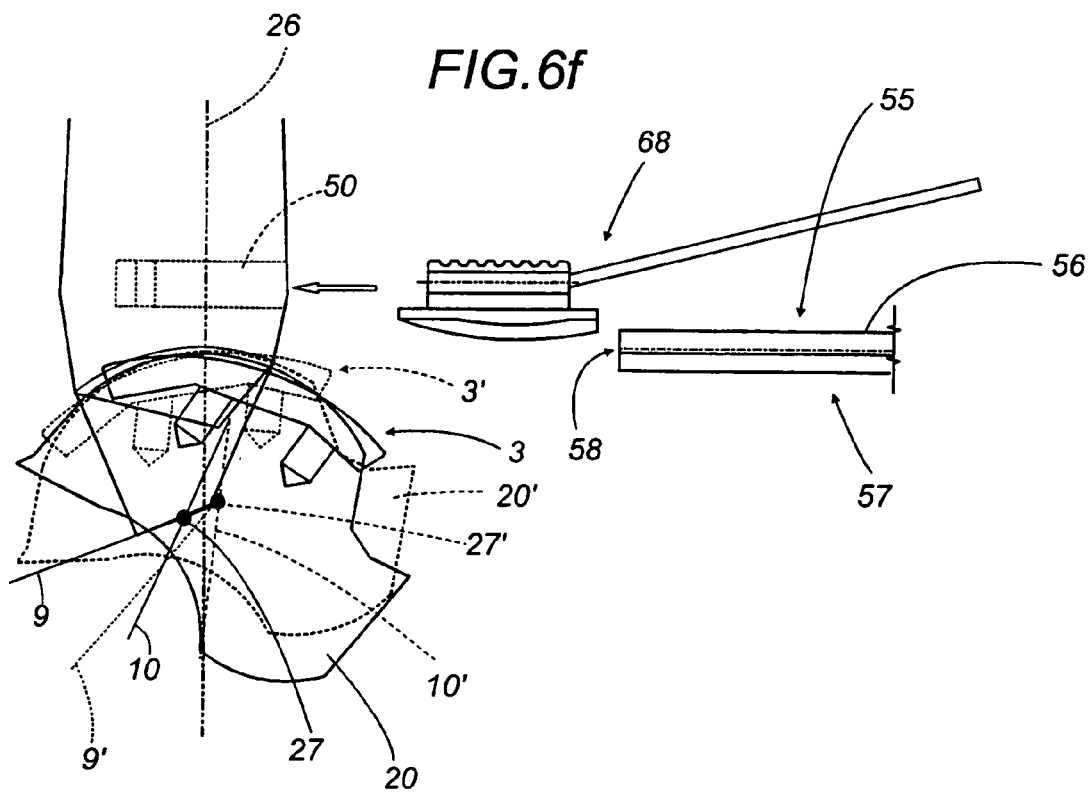
Figure 6G:
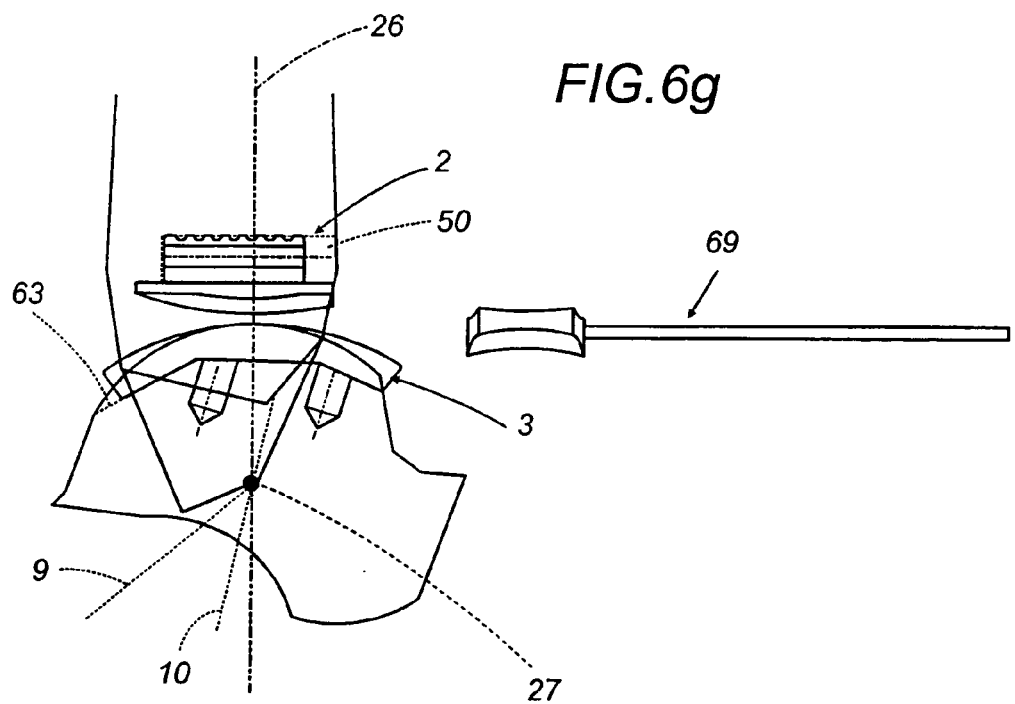
Figure 6H:
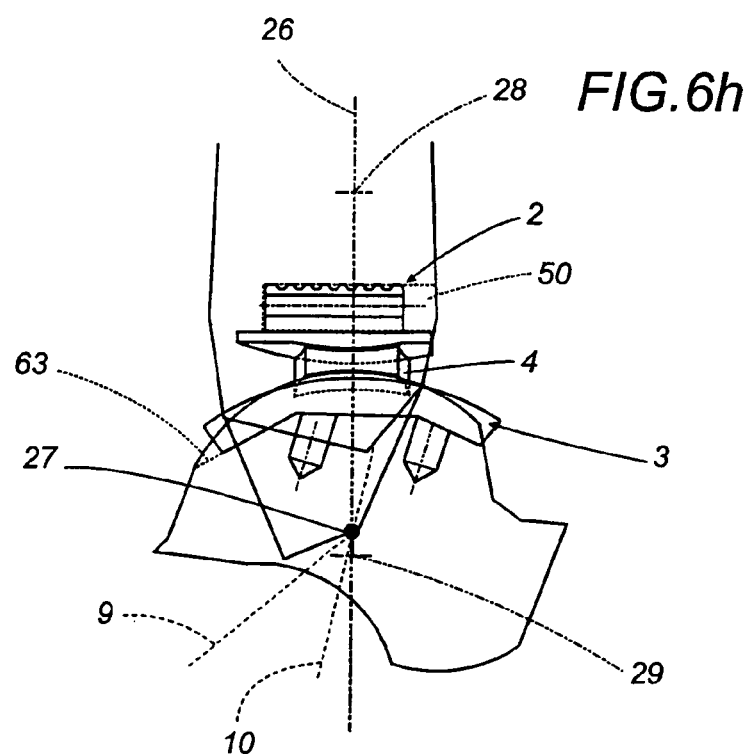

In accordance with FIGS. 6*a* through 6*h*, the implantation method essentially comprises the phases listed below.

a) Two antero-posterior cuts 61, 62 are first made on the distal part of the tibia 11 and on the part proximal of the talus 20 (FIG. 6*a*). The talar component 3 should cover the talus bone 20 as a shell, but it should be located to have the center of curvature 29 of the circular upper arc 6 in the same antero-posterior position as the axis of rotation 27 of the joint when it is in its neutral position; this position being determined, as stated above, by the sagittal configuration of the two ligaments 9, 10 (FIG. 3*b*).

b) Therefore the optimal antero-posterior position for the talar component 3 should be sought with a step-by-step procedure using a talar template 65. For the meniscal bearing 4 to be able to slide on both the components 2, 3 guided by the isometric rotation of the two ligaments 9, 10, the gap between the two bone-anchored components 2, 3 must remain constant for every position of the joint. Starting from an initial, however small, trial depth of the anterior talar chamfer 64, a trial talar template 65 is inserted from the front (FIG. 6*b*). The trial talar template 65 has exactly the same three-dimensional shape as the final talar component 3 except for the lack of all its posterior parts located inferiorly to the surface 16, i.e. to the cutting surface 62.

c) In this temporary position, the gap between the tibial flat cut 61 and the talar template 65 is measured in both maximal plantar-flexion and maximal dorsi-flexion positions (FIG. 6*c*) (see the different corresponding continuous and dashed lines, as well as the homologous numerical references, shown without and with apostrophes), using a series of appropriate flat-top gap-gauges 51 (FIG. 5*a*), able to measure the distance between the base and the top of the gap. These gap-gauges are 10–15 cm long plastic rods of different thicknesses 54 (from 1 to 15 mm, step 1 mm) having a constant section with an upper flat shape 52 to slide on the tibial flat cut 61, and with a lower generally convex shape 53 complementary with the corresponding frontal shape of the talar component 3, i.e. of the sulcus 14, 15 (as in FIG. 2). With the series of gap gauges 51, the surgeon finds the gauge that best fits in the gap interposed between the tibial cut 61 and the talar template 65, without excessive tensioning or excessive slackening of the two ligaments 9, 10. If the dorsi-plantar-gaps are not equal, the surgeon removes the talar template 65, removes a greater quantity of anterior talar bone on the chamfer 64, inserts the template 65 again, and carries out the two gap measurements in dorsi- and plantarflexion anew. This procedure is repeated until the dorsi- and plantar flexion gaps are exactly equal.

d) After, and only after, the talar template 65 can be used to guide the drill to obtain the talar holes 66 for the pins 19*a*, 19*b*, and to make the posterior chamfer 63 (FIG. 6*d*) for a better anchoring of the talar component 3 to the talus bone 20. The talar template 65 is then definitively removed and replaced with the final metal talar component 3. This is the location for the component which will assure the restoration of the original conditions of proper tensioning the ligament fibers 9, 10.

e) Once the talar component 3 is implanted, its position also determines univocally the medio-lateral as well as the antero-posterior location of the tibial component 2 (FIG. 6e). Using a guiding element 70 for the drill screw, having a lower surface 67 capable of being fitted on the talar sulcus 14, 15, the two holes 50 for the cylindrical bars 12 of the tibial component 2 are drilled with a drill bit whose penetration in the tibial bone is stopped at a shallow depth.

f) A procedure similar to that shown in FIG. 6c is suggested here (FIG. 6f) (see the different continuous line and dashed line positions, as well as the homologous numerical references, shown without and with apostrophe) to prepare the correct final antero-posterior position for the tibial component 2. The two holes 50 are made progressively deeper by means of small successive stepped advances of the bit. Again, for the meniscal bearing 4 to slide on both the bone-anchored components 2, 3 guided by the isometric rotation of the two ligaments 9, 10, it is necessary that the gap between these components 2, 3 remain constant in all positions of the joint. If the gap changes during flexion, the replaced joint can be either rigid or lax in one flexion position. Starting from an initial, however small, trial depth of the holes 50 of the distal tibia 2, the trial tibial component 68 is inserted from the front to the bottom of the holes. In this temporary position for the trial tibial component 68, the gap between the trial tibial component 68 and the talar component 3 is measured in both maximal dorsi- and maximal plantar-positions, using a different series of gap-gauges 55 (FIG. 5b). These latter are 10–15 cm long plastic rods of different thickness 58 (from 1 to 15 mm, step 1 mm) having a constant section with an upper concave shape 56 with the same radius of curvature 21 of the tibial arc 5, and with a lower generally convex shape 57, complementary to the corresponding frontal shape of the talar component 3, i.e. to the sulcus 14, 15 of FIG. 2. From the series of gap-gauges 55, the surgeon obtains indications for choosing the gauge that best fits between the trial tibial 68 and talar component 3 without tensioning or slackening the two ligaments 9,10. The declared thickness 58 of the selected gap gauge will give the measure of the gap: this should be done in both maximal dorsi- and maximal plantar-position (FIG. 6f). Starting from an anterior misplacement of the trial tibial component 68, the dorsal gap is expected to be smaller than the plantar gap. The surgeon should then remove the trial component, make deeper holes 50, insert the trial component again, and carry out the gap measurement until the dorsal and plantar gap are exactly the same. As the holes 50 are made deeper, the difference is expected to get smaller. When the dorsal- and plantar gaps are equal and the holes 50 have reached the exact maximum depth, the final tibial component 2 can be definitively implanted.

g) Then and only then can the trial tibial component 68 be removed and definitively replaced with the final metal component 2 (FIG. 6g). This is the location for the component which should enable the restoration of the original pattern of proper tensioning of the ligaments 9, 10. Once the final tibial and talar components 2, 3 are implanted in the correct absolute position, they define the location of the final meniscal bearing component 4. The last test to be performed is the identification of the best thickness of the meniscal bearing 4 for the best restoration of the original pattern of tensioning of the two ligaments 9, 10 throughout the whole range of motion. This procedure can be easily performed with trial meniscal bearings 69 in a series of different thicknesses. These are polyethylene meniscal bearings with exactly the same three-dimensional shape as the meniscal bearing 4, but provided with a handhold to facilitate trials and measurements.

h) The final configuration of the tibial 2, talar 3, and meniscal bearing 4 components in their appropriate locations is reported in FIG. 6h.

The invention thus conceived is clearly suitable for industrial application; moreover, it can be subject to numerous modifications and variations, without thereby departing from the scope of the inventive concept. Furthermore, all components can be replaced by technically equivalent elements.

What is claimed is:

1. A prosthetic ankle joint device for articulating segments comprising:
    a first component (2) having a first articular bearing surface (5), the first component (2) adapted to engage a first tibial bone segment (11);
    a second component (3) having a second articular bearing surface (6) opposite to the first bearing surface (5) of the first component (2), the second component (3) adapted to engage a second tarsal bone segment (20); and
    a third component (4) interposed to the first (2) and the second component (3), having two articular third and fourth bearing surfaces (7, 8) whose individual forms are complementary to said first and second articular surfaces (5, 6) of the first (2) and of the second (3) components, said third and fourth articular bearing surfaces (7, 8) being freely slidable, both in a sagittal plane and a frontal plane transverse to the sagittal plane, and individually non-captively engaged;
    said first articular bearing surface (5) and said second articular bearing surface (6) being both shaped not reproducing natural corresponding shapes of said articulating segments;
    the first and third (5, 7) and the second and fourth (6, 8) articular bearing surfaces being shaped complementarily and mutually to allow a non-fixed axis of rotation of the articulation to be reproduced while maintaining full congruence, wherein the first articular surface of said first component and the third articular surface of said third component complementary thereto are each shaped partly spherically with equal radii of curvature.

2. A prosthetic ankle joint device according to claim 1, wherein the first and third (5, 7) and the second and fourth (6, 8) articular bearing surfaces are shaped complementarily and mutually to allow the non-fixed axis of rotation of the articulation to be reproduced based on the typical isometric rotation kinematics of some ligament fibers (9, 10) of the natural joint in the unloaded state, therefore optimally designed from the subject-specific geometry of said ligament fibers (9, 10).

3. A prosthetic ankle joint device as set forth in claim 1, wherein the first component (2) has a generally convex first articular bearing surface (5); the second component (3) has an articular bearing second surface (6) that is generally convex in a sagittal plane and partly concave in a frontal plane; and the third component (4) has two articular third and fourth bearing surfaces (7, 8) with front-to-back disposition and with individual shapes that are complementary to said first and second articular surfaces (5, 6) of the first (2)

and of the second (3) component, said third component (4) being situated between said first and second component (2, 3) with the said complementary first and third (5, 7) surfaces and said complementary fourth and second (8, 6) surfaces coupled in the said freely sliding and individually unconstrained manner.

4. A prosthetic ankle joint device as claimed in claim 1, wherein the second articular surface of said second component and the fourth articular surface of said third component complementary thereto are each partly anticlastic surfaces and have equal curvatures.

5. A prosthetic ankle joint device as claimed in claim 1, wherein said first and second components each present a wholly metallic construction, and said third component is wholly constructed of plastic material.

6. A prosthetic ankle joint device (1) for an articulation with non congruent shape between two articular bone segments (11, 20) having articular surfaces respectively with individually concave and convex curvatures with greater and lesser radii of curvatures, said device (1) comprising a first component (2) having a partially spherical convex first articular bearing surface (5) suitable for being anchored to a first of said bone segments (11) to replace said concave surface; a second component (3) having a second anticlastic articular bearing surface (6) that is convex in a sagittal plane and partly concave in a frontal plane, and suitable for being anchored to a second of said bone segments (20) to replace said convex surface; and a third component (4) having two articular third and fourth bearing surfaces (7, 8) in front-to-back disposition, the third surface (7) presenting a partially spherical concave shape with curvature equal to the convex first surface (5) of the first component (2), and the fourth surface (8) being a partly anticlastic surface with curvatures equal to the curvatures of the second articular bearing surface (6) of the second component (3); said third component (4) being interposed to the first (2) and the second component (3), having said two articular third and fourth bearing surfaces (7, 8) whose individual forms are substantially complementary to said first and second articular surfaces (5, 6) of the first (2) and of the second (3) components, said third and fourth articular bearing surfaces (7, 8) being freely slidably and individually non-captively engaged.

7. A prosthetic ankle joint device as claimed in claim 3 wherein each of said components (2, 3, 4) presents a single-piece construction.

8. A prosthetic ankle joint device for the human ankle articulation for an articulation of incongruent shape between two bone segments (11, 20) having articular surfaces respectively with individually concave and convex curvatures with greater and lesser radii of curvature, said device (1) comprising a tibial component (2) able to be anchored to the tibia (11) and defining a partially spherical convex first articular bearing surface (5); a talar component (3) able to be anchored to the talus (20) and defining a partly anticlastic second articular bearing surface (6); and a meniscal component (4) defining two articular third and fourth bearing surfaces (7, 8) in front-to-back disposition, the third surface (7) presenting a partially spherical concave shape with curvature equal to the convex first surface (5) of the first component (2), and the fourth surface (8) being a second partly anticlastic surface with curvatures equaling those of said talar component (3); said meniscal component (4) being situated and maintained between the tibial (2) and talar (3) components, having said two articular third and fourth bearing surfaces (7, 8) whose individual forms are substantially complementary to said first and second articular surfaces (5, 6) of the tibial (2) and of the talar (3) components, said third and fourth articular bearing surfaces (7, 8) being freely slidably and individually non-captively engaged.

9. A prosthetic ankle joint device for articulating segments comprising:
   a first component (2) having a first articular bearing surface (5), the first component (2) adapted to engage a first tibial bone segment (11);
   a second component (3) having a second articular bearing surface (6) opposite to the first bearing surface (5) of the first component (2), the second component (3) adapted to engage a second tarsal bone segment (20); and
   a third component (4) interposed to the first (2) and the second component (3), having two articular third and fourth bearing surfaces (7, 8) whose individual forms are substantially complementary to said first and second articular surfaces (5, 6) of the first (2) and of the second (3) components, said third and fourth articular bearing surfaces (7, 8) being freely slidable, both in a sagittal plane and a frontal plane transverse to the sagittal plane, and individually non-captively engaged;
   said first articular bearing surface (5) and said second articular bearing surface (6) being both shaped not reproducing natural corresponding shapes of said articulating segments;
   the first and third (5, 7) and the second and fourth (6, 8) articular bearing surfaces being shaped complementarily and mutually to allow a non-fixed axis of rotation of the articulation to be reproduced while maintaining full congruence wherein:
   the first component (2) has a generally convex first articular bearing surface (5); the second component (3) has an articular bearing second surface (6) that is generally convex in a sagittal plane and partly concave in a frontal plane; and the third component (4) has two articular third and fourth bearing surfaces (7, 8) with front-to-back disposition and with individual shapes that are complementary to said first and second articular surfaces (5, 6) of the first (2) and of the second (3) component, said third component (4) being situated between said first and second component (2, 3) with said complementary first and third (5, 7) surfaces and said complementary fourth and second (8, 6) surfaces coupled in the said freely sliding and individually unconstrained manner; and
   wherein the first articular surface of said first component and the third articular surface of said third component complementary thereto are each shaped partly spherically with equal radii of curvature.

10. A prosthetic ankle joint device as claimed in claim 3, wherein the second articular surface of said second component and the fourth articular surface of said third component complementary thereto are each partly anticlastic surfaces and have equal curvatures.

11. A prosthetic ankle joint device as claimed in claim 3, wherein said first and second components each present a wholly metallic construction, and said third component is wholly constructed of plastic material.

* * * * *

UNITED STATES PATENT AND TRADEMARK OFFICE
CERTIFICATE OF CORRECTION

PATENT NO. : 6,926,739 B1
DATED : August 9, 2005
INVENTOR(S) : John J. O'Connor et al.

It is certified that error appears in the above-identified patent and that said Letters Patent is hereby corrected as shown below:

<u>Title page,</u>
Item [73] Assignees, should read -- John J. O'Connor and Istituti Orthopedici Rizzoli --.

Signed and Sealed this

Eighth Day of November, 2005

JON W. DUDAS
*Director of the United States Patent and Trademark Office*